United States Patent
Pinkos et al.

(10) Patent No.: US 7,098,349 B2
(45) Date of Patent: Aug. 29, 2006

(54) METHOD FOR PRODUCING TETRAHYDROFURAN

(75) Inventors: Rolf Pinkos, Bad Dürkheim (DE); Stefan Käshammer, Schifferstadt (DE); Volkmar Menger, Neustadt (DE); Martin Haubner, Eppelheim (DE); Peter Groll, Dannstadt-Schauernheim (DE); Stephan Schlitter, Limburgerhof (DE); Klaus-Peter Pfaff, Friedelsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 59 days.

(21) Appl. No.: 10/524,851

(22) PCT Filed: Jul. 30, 2003

(86) PCT No.: PCT/EP03/08403

§ 371 (c)(1),
(2), (4) Date: Feb. 18, 2005

(87) PCT Pub. No.: WO2004/026853

PCT Pub. Date: Apr. 1, 2004

(65) Prior Publication Data

US 2006/0122365 A1    Jun. 8, 2006

(30) Foreign Application Priority Data

Aug. 20, 2002  (DE) ................................ 102 37 954

(51) Int. Cl.
*C07D 307/02*    (2006.01)

(52) U.S. Cl. ..................................................... 549/509
(58) Field of Classification Search ................. 549/509
See application file for complete search history.

(56) References Cited

U.S. PATENT DOCUMENTS

| 5,596,074 | A  | 1/1997  | Bloxham et al. |
| 5,641,857 | A  | 6/1997  | Dostalek et al. |
| 6,201,137 | B1 | 3/2001  | Nakaoka et al. |
| 6,316,640 | B1 | 11/2001 | Fischer et al. |

FOREIGN PATENT DOCUMENTS

| DE | 29 16 653 A1      | 11/1980 |
| DE | 42 05 984 C1      | 5/1993  |
| JP |     126080 A      | 6/1986  |
| WO | WO-03/099905 A1   | 12/2003 |

OTHER PUBLICATIONS

K. Weissermel, H.-J. Arpe Industrielle Organ. Chemie, VCH, Weinheim 1994, p. 111.
Chemie 17 (1977) pp. 353-357 and 19 (1979) p. 308.
Handbuch der Praparativen Anorgan. Chemie, III, pp. 1774-1784 Enke (1981).
F. Ehrenberger, Quantitative Organ. Elementaranalyse 37, p. 382.
Database WPI, Derwent Publ. Ltd., XP002261198 (JP 61 126080).
Database WPI, Derwent Publ. Ltd. XP002261199 (CN 1 272 495).

*Primary Examiner*—Bernard Dentz
(74) *Attorney, Agent, or Firm*—Connolly Bove Lodge & Hutz LLP; Matthew J. Mason

(57) ABSTRACT

The invention relates to a process for the continuous preparation of THF by reaction of a 1,4-butanediol-containing reaction mixture over a heteropolyacid catalyst which has not been predried, wherein the reaction mixture comprises 2-(4-hydroxybutoxy)tetrahydrofuran.

16 Claims, No Drawings

METHOD FOR PRODUCING TETRAHYDROFURAN

CROSS REFERENCE TO RELATED APPLICATION

The present application is a National Stage application of PCT/EP2003/008403, filed Jul. 30, 2003, which claims priority from German Patent Application No. DE 102 37 954.8, filed Aug. 20, 2002.

The present invention relates to a process for the continuous preparation of tetrahydrofuran by cyclization of 1,4-butanediol.

Processes for preparing THF from 1,4-butanediol have been known for a long time. K. Weissermel, H.-J. Arpe, Industrielle Organische Chemie, VCH Verlagsgesellschaft, D-69451 Weinheim, 1994, page 111, describe the conversion of 1,4-butanediol into THF by elimination of water with addition of phosphoric acid, sulfuric acid or acid ion exchangers. Here, the 1,4-butanediol admixed with acid is heated and further 1,4-butanediol is added in an amount corresponding to the amount of THF/water distilled off.

JP-A 61-126 080 discloses the heteropolyacid-catalyzed cyclization of 1,4-butanediol to THF. In addition, Example 4 describes the conversion of 1,4-butanediol diacetate into THF with addition of water. The conversions to THF are less than 100% in all examples, so that starting compound is always still present toward the end of the reaction. This is disadvantageous in the case of industrial-scale reactions, since the unreacted starting material either has to be discarded or recirculated in a costly fashion. The examples indicate that drying of the heteropolyacid is necessary before it can be used in the cyclization. In addition, the described use of at least 5% by weight of heteropolyacid, based on the alcohol used, is very costly.

A further disadvantage of this process for preparing THF is that the 1,4-butanediol which is usually used has to be purified before use. Secondary components in the butanediol which usually have to be removed in this purification are 2-(4-hydroxybutoxy)tetrahydrofuran, viz. a cyclic acetal of 4-hydroxybutyraldehyde and 1,4-butanediol (hereinafter referred to as acetal) and dimers, oligomers or polymers of butanediol (polytetrahydrofuran, hereinafter referred to as polyTHF) and also acetates and diacetates of polyTHF.

These secondary components can adversely affect the continuous preparation of THF. Thus, the acetal decomposes into 2,3-dihydrofuran and 1,4-butanediol under acidic conditions, and the 2,3-dihydrofuran polymerizes very readily in the presence of acids. These polymers can accumulate and can result in a loss of product and catalyst when they are discharged. In the presence of acid and water, the acetal is hydrolyzed to form 1,4-butanediol and 4-hydroxybutyraldehyde, and the latter is likewise able to polymerize.

The secondary components based on polytetrahydrofuran (polyTHF) or polyTHF diacetate and monoacetate can likewise lead to accumulation of polymers. A prerequisite for an industrially satisfactory operation time is thus a dissociation of the polyTHF derivatives under the reaction conditions.

The purification of 1,4-butanediol is usually carried out by means of a complicated, multistage distillation in which undesirable low-boiling and/or high-boiling constituents, including water, are separated off. This water-free pure butanediol is subsequently converted into THF, with water and undesirable by-products being formed. The THF obtained as product therefore has to be once again purified by multistage distillation after the reaction. Thus, comparable, complicated purification and separation steps have to be carried out twice.

It is an object of the present invention to provide a process for preparing THF from 1,4-butanediol in the presence of heteropolyacids, which process gives virtually complete conversion and in which the 1,4-butanediol-containing reaction mixture used does not have to be prepurified and the formation of appreciable amounts of by-product is avoided. In addition, the heteropolyacid catalyst should neither have to be predried nor have to be used in large amounts.

The achievement of this object starts out from a process for preparing THF by reaction of a 1,4-butanediol-containing reaction mixture over a heteropolyacid catalyst which has not been predried.

The process of the present invention has the advantage that the 1,4-butanediol-containing reaction mixtures used do not have to be prepurified before the reaction to form THF. 1,4-Butanediol is cyclized in the presence of acetal and/or polyTHF and/or its monoesters or diesters without appreciable amounts of by-product being formed. The complicated prepurification thus becomes unnecessary, as does predrying of the catalyst and the use of large amounts of catalyst, so that considerable costs can be saved and an economical process can be made available.

The 1,4-butanediol-containing reaction mixtures used in the reaction can be obtained by known methods.

Thus, for example, it is possible to use a 1,4-butanediol-containing reaction mixture which is obtained by the Reppe process from acetylene and formaldehyde and subsequent hydrogenation of the 1,4-butynediol formed, or by acetoxylation or chlorination of butadiene. The 1,4-butanediol-containing reaction mixtures obtained by the Reppe process generally contain from 50 to 3000 ppm of acetal.

It is also possible to use the crude product from the hydrogenation of a compound selected from among maleic acid, maleic monoesters, maleic diesters, maleic anhydride, and an intermediate formed in the hydrogenation as 1,4-butanediol-containing reaction mixture. Such intermediates are, for example, succinic anhydride, γ-butyrolactone, succinic acid or succinic diesters. Preference is given to using the crude product from the hydrogenation of maleic diesters or maleic acid in the reaction to form THF.

The hydrogenation can be carried out in a known manner in the gas phase or liquid phase. For example, dimethyl maleate can be hydrogenated in the gas phase under superatmospheric pressure and at elevated temperature over a catalyst, e.g. copper chromite. The crude hydrogenation product obtained, which is used as feed in the reaction of the present invention, generally comprises 5–85% by weight of butanediol and 15–95% by weight of alcohol, preferably from 10 to 70% by weight of butanediol and from 15 to 70% by weight of alcohol, particularly preferably from 15 to 60% by weight of butanediol and from 15 bis 50% by weight of alcohol. In addition, products such as γ-butyrolactone or succinic diesters can be present in amounts up to, for example, 30% by weight. The contents of γ-butyrolactone or succinic diesters are generally not critical for the process. Furthermore, water can be present in an amount of generally less than 5% by weight, preferably less than 2% by weight, particularly preferably less than 1% by weight, together with small amounts of further compounds. It is possible for THF to be present in the crude hydrogenation product, with the THF content not being critical to the process and being able to be, for example, from 10 to 30% by weight.

In place of the total crude hydrogenation product, it is possible for only a substream of the crude hydrogenation product to be passed to the reaction to form THF. The reaction product of the reaction to form THF can be fed into the same work-up columns as the substream of the crude hydrogenation product which has not been reacted further, since both contain similar impurities and by-products. In this way, it is not necessary to operate different apparatuses for comparable separation tasks.

Furthermore, a polyTHF-containing reaction mixture can also be used as 1,4-butanediol-containing reaction mixture which further comprises not only acetal but also polyTHF and/or its monoacetate or diacetate. Such polyTHF-containing reaction mixtures are prepared by polymerization of THF over solid acidic catalysts, as described, for example, by T. Setoyama et al., Catalysis Today 73 (2002), pages 29–37. PolyTHF and/or polyTHF monoacetate and diacetate streams are obtained in the polymerization as a result of by-product streams, purge streams and start-up and shut-down processes, and these have to be burnt if they cannot be redissociated into THF and, if applicable, acetic acid. The streams can be used in the process of the present invention as 1,4-butanediol-containing reaction mixture and comprise from 0 to 95% by weight of polyTHF and/or polyTHF monoacetate or diacetate, based on the 1,4-butanediol-containing reaction mixture, but generally contain not more than 50% by weight of polyTHF and/or its derivatives. The polyTHF or its monoesters or diesters have mean molar masses of from 150 to 5000.

For the purposes of the present patent application, the term "mean molecular weight" or "mean molar mass" refers to the number average molecular weight $M_n$ of the polymers present in the polymerization product formed.

The reaction of the 1,4-butanediol-containing reaction mixture is carried out at from 80 to 300° C., preferably from 140 to 250° C., particularly preferably from 150 to 220° C. It is carried out in a pressure range from 0.1 to 15 bar, preferably from 0.5 to 10 bar, particularly preferably from 0.8 to 5 bar.

Heteropolyacids are used as catalysts for the reaction of the 1,4-butanediol-containing reaction mixture.

Heteropolyacids used for the purposes of the present invention are inorganic polyacids which, in contrast to isopolyacids, have at least two different central atoms. Heteropolyacids are formed from in each case weak polybasic oxo acids of a metal such as chromium, molybdenum, vanadium or tungsten and a nonmetal such as arsenic, iodine, phosphorus, selenium, silicon, boron or tellurium as partially mixed anhydrides. Examples are dodecatungstophosphoric acid $H_3(PW_{12}O_{40})$ or decamolybdophosphoric acid $H_3(PMo_{12}O_{40})$. The heteropolyacids can also contain actinides or lanthanides as second central atom (cf. Z. Chemie 17 (1977), pages 353 to 357, or 19 (1979), 308). The heteropolyacids can generally be described by the formula $H_{8-n}(Y''M_{19}O_{40})$ where n=valence of the element Y (e.g. boron, silicon, zinc) (cf. Heteropoly- and Isopolyoxometalates, Berlin; Springer 1983). The heteropolyacids mentioned in JP-A 61-126 080, which is hereby expressly incorporated by reference, are also suitable as catalysts for the process of the present invention. Particularly useful catalysts for the process of the present invention are phosphotungstic acids and phosphomolybdic acids such as dodecamolybdophosphoric acid $(H_3PMo_{12}O_{40}.nH_2O)$, octadecamolybdodiphosphoric acid $(H_6P_2Mo_{18}O_{62}.11\ H_2O)$, dodecatungstophosphoric acid $(H_3PW_{12}O_{46}.nH_2O)$ and hexamolybdohexatungstophosphoric acid $(H_3PMo_6W_6O_{40}.nH_2O)$.

Of course, it is also possible to use mixtures of heteropolyacids. Owing to their ready availability, particular preference is given to using dodecatungstophosphoric acid and dodecamolybdophosphoric acid in the process of the present invention.

According to the present invention, preference is given to using the free heteropolyacids, but it is also possible to employ their salts, in particular their alkali metal and alkaline earth metal salts, as catalysts. The heteropolyacids and their salts are known compounds and can be prepared by known methods, for example by the methods described by Brauer (editor): Handbuch der Präparativen Anorganischen Chemie, volume III, pp. 1774–1784, Enke, Stuttgart, 1981, or by the method of Top. Curr. Chem. 76, 1 (1978).

The heteropolyacids prepared in this way and also the corresponding commercial products contain from 20 to 40 mol of water/mol of heteropolyacid and are used undried for the purposes of the present invention. No water in addition to the water of crystallization of the heteropolyacid is added to the 1,4-butanediol-containing reaction mixture. According to the present invention, less than 1% by weight of heteropolyacid, based on the 1,4-butanediol-containing reaction mixture, is used.

It has been found to be advantageous to keep the content of heteropolyacid below 1% by weight. Preference is given to using 50–10000 mg, particularly preferably from 500 to 5000 mg, of heteropolyacid per kg of 1,4-butanediol-containing reaction mixture. Surprisingly, the reaction rate is high despite the low content of heteropolyacids. An industrially more usual and better measure of the amount of heteropolyacid used in a continuous process is the total amount of heteropolyacid per kg of butanediol reacted, also referred to as input number. The total amount of heteropolyacid per kg of butanediol reacted is from 0.1 to 200 mg, preferably from 0.5 to 100 mg, particularly preferably from 1 to 50 mg.

It has been recognized according to the present invention that the process of the present invention proceeds particularly economically with long catalyst operating lives when the 1,4-butanediol-containing reaction mixture contains less than 1 ppm of basic nitrogen component. The amount of nitrogen component present can be determined by the method described by F. Ehrenberger in Quantitative organische Elementaranalyse, ISBN 3-527-28056—chapter 37, page 382.

In the industrial implementation of the process of the present invention, a metallic reactor is generally used. Since a metallic surface can release metal ions, particularly when acids such as acetic acid from the dissociation of polyTHF acetates are present, deactivation of the heteropolyacid used according to the present invention by metal ions occurs over the course of time. This effect can also occur as a result of amine-containing components in the feed streams. To maintain the activity of the heteropolyacid in such a case, the liquid contents of the reactor can be passed over a solid which is able to absorb cations, e.g. of irons, nickel, chromium and aluminum and also ammonium ions. Such solids are, for example, typical organically based, commercially available ion exchangers in protonated form. Examples are the commercial Lewatit products from Bayer AG, Leverkusen, Amberlite products from Röhm and Haas GmbH, Darmstadt, or Nafion from E.I. du Pont de Nemours. It is of course also possible to use inorganic ion exchangers such as the commercial Deloxan products from Degussa AG, Hanau, aluminas and zeolites in the H form.

The THF obtained by the process of the present invention can be used for further purposes, e.g. as solvent. The THF obtained by the process of the present invention is particularly preferably used for preparing polyTHF or its monoesters or diesters.

The THF obtained by the process of the present invention is particularly preferably subjected to a hydrogenation before being used in the polymerization to form polyTHF or its monoesters or diesters.

Here, the THF is hydrogenated in a manner known per se, e.g. over Ni, Pd or Cu-containing catalysts. It has surprisingly been found that in this way the polymerization, as is described, for example, in DE 2 916 653 A1, is associated with longer catalyst operating lives and lower color numbers of the product.

The conversion of the 1,4-butanediol present in the reaction mixture into THF is generally from 99 to 100%. Thus, the crude product after the conversion of 1,4-butanediol into THF (crude cyclization product) has a composition which corresponds essentially to that of the feed except that the 1,4-butanediol present in the feed has been converted into THF and water. The crude cyclization product generally comprises THF, water of reaction and small amounts of 2,3-dihydrofuran.

On the basis of the composition of the crude cyclization product, it is clear that no appreciable formation of by-products, e.g. ethers formed by intramolecular reaction, occurs in the conversion of 1,4-butanediol-containing reaction mixtures into THF in the presence of heteropolyacids.

The crude cyclization product can be worked up by distillation using methods known to those skilled in the art. EP-B 0 485 484 describes various methods of isolating THF from mixtures comprising THF, one or more low-boiling alcohols and water. Thus, the isolation can be carried out by, for example, extractive distillation with addition of a further component such as 1,4-butanediol, water, ethylene glycol or other components. EP-B 0 485 484 also describes a process for recovering THF from the mixtures mentioned, which comprises two successive distillations of which the first is carried out at a lower pressure than the second, and a condensation carried out between the distillations. The mixture obtained from the second distillation, which is enriched in by-products, is in turn condensed together with the stream from the first distillation, and the pure THF obtained in the second distillation is separated off.

The following examples illustrate the invention.

EXAMPLES

The percentages of butanediol or the crude reaction products are GC percentages by area determined by gas chromatography.

The 1,4-butanediol used in the examples is a commercial product from BASF AG/Ludwigshafen and had the following composition: 99.8% of 1,4-butanediol, 800 ppm of acetal, balance predominantly 2-methylbutanediol.

Example 1

A 250 ml glass flask was half filled with about 100 g of 1,4-butanediol which contained 800 ppm of acetal and whose content of basic nitrogen components was <1 ppm. 100 mg of commercial dodecatungstophosphoric acid which had not been dewatered were added thereto. The mixture was heated to 175–180° C. After a short time, a mixture of THF and water which additionally contained 1000 ppm of 1,4-butanediol, 450 ppm of 3-methyltetrahydrofuran and about 300 ppm of 2,3-dihydrofuran distilled off. Fresh butanediol was continuously fed in by means of a pump at a rate corresponding to that at which product distilled off (about 15 g/h). The product was discharged entirely via the gas phase, i.e. virtually no high boilers were discharged via the liquid phase. After 500 hours of operation, the composition of the crude reaction product was still the same as at the beginning of the reaction. The productivity also corresponded to that during the first hour. Thus, 7.5 kg of butanediol were able to be reacted in 500 hours of operation using only 100 mg of heteropolyacid, without the activity of the heteropolyacid having suffered during this time, i.e. 13.3 mg of heteropolyacid are required per kg of butanediol.

Example 2

In a manner analogous to Example 1, 1,4-butanediol was reacted under the conditions of Example 1. After 48 hours, the feed to the reaction was changed to a mixture comprising 80% by weight of 1,4-butanediol, 13% of THF and polyTHF diacetates and monoacetates having a mean molecular weight of 460. At a reaction temperature of 180° C., GC analysis of the product after a further 96 hours indicated the presence of THF and water together with 300 ppm of 1,3-dihydrofuran, 500 ppm of 1,4-butanediol, 900 ppm of 3-methyltetrahydrofuran and some unknown compounds present in subordinate amounts. The catalyst productivity was as at the beginning.

Example 3

THF prepared as described in Example 2 was washed twice with 40% strength aqueous sodium hydroxide solution and subsequently distilled at 1013 mbar and a temperature at the top of about 65° C. The THF obtained in this way contained 90 ppm of 2,3-dihydrofuran. 500 g of this THF were polymerized in a manner analogous to Example 1b) of DE 2 916 653. The initial conversion of about 34% decreased after only a few hours. After 24 hours, the experiment was stopped. The conversion had dropped to 30% and the polymerization product had a yellow color.

Example 4

1000 g of a THF which had been purified as described in Example 3 by treatment with aqueous sodium hydroxide and subsequent distillation was hydrogenated at 10 bar, 60° C., over a catalyst having the following composition (oxidic): 21.5% of NiO, 7.3% of CuO, 2.0% of $Mn_3O_4$, 1.2% of $H_3PO_4$, balance $SiO_2$, which had previously been activated by means of hydrogen at 180° C. The THF was subsequently polymerized as in Example 3. After an operating time of 48 hours, the catalyst displayed no decrease in the activity and the reaction products were colorless.

Example 5

Example 2 was repeated, but with addition of 50 ml of V4A wire spirals (1.4571) (simulation of a stainless steel reactor). After 700 hours, the catalyst activity was about 40% of the initial activity. The reaction mixture was then cooled to about 25° C. and the liquid phase was filtered through 50 ml of an acid cation exchanger (Amberlite-IR-120) and used again under the original reaction conditions. The initial activity was restored.

We claim:

1. A process for the continuous preparation of THF comprising reaction of a 1,4-butanediol-containing reaction mixture over a heteropolyacid catalyst which has not been predried, wherein the reaction mixture comprises less than 1 ppm of basic nitrogen components and 2-(4-hydroxybutoxy)tetrahydrofuran.

2. The process according to claim 1, wherein the reaction mixture comprises at least one component selected from the group consisting of polytetrahydrofuran, monoacetates of polytetrahydrofuran, and diacetates of polytetrahydrofuran.

3. The process according to claim 1, wherein less than 1% by weight of heteropolyacid, based on the reaction mixture, is added.

4. The process according to claim 1, wherein the reaction is carried out at from 80 to 300° C.

5. The process according to claim 1, wherein the reaction is carried out in a pressure range from 0.5 to 10 bar.

6. The process according to claim 1, wherein the reaction mixture is passed over a cation exchanger after the activity decreases.

7. The process according to claim 2, wherein less than 1% by weight of heteropolyacid, based on the reaction mixture, is added.

8. The process according to claim 2, wherein the reaction is carried out at from 80 to 300° C.

9. The process according to claim 3, wherein the reaction is carried out at from 80 to 300° C.

10. The process according to claim 2, wherein the reaction is carried out in a pressure range from 0.5 to 10 bar.

11. The process according to claim 3, wherein the reaction is carried out in a pressure range from 0.5 to 10 bar.

12. The process according to claim 4, wherein the reaction is carried out in a pressure range from 0.5 to 10 bar.

13. The process according to claim 2, wherein the reaction mixture is passed over a cation exchanger after the activity decreases.

14. The process according to claim 3, wherein the reaction mixture is passed over a cation exchanger after the activity decreases.

15. The process according to claim 4, wherein the reaction mixture is passed over a cation exchanger after the activity decreases.

16. The process according to claim 5, wherein the reaction mixture is passed over a cation exchanger after the activity decreases.

* * * * *